United States Patent [19]

Swenson et al.

[11] 4,439,422

[45] Mar. 27, 1984

[54] GROUP B STREPTOCOCCUS ANTIGENS AND VACCINES

[75] Inventors: Robert M. Swenson; Gerald D. Shockman, both of Philadelphia; Toby K. Eisenstein, Wyndmoor, all of Pa.; Roberta B. Carey, Princeton Junction, N.J.

[73] Assignee: Research Corporation, New York, N.Y.

[21] Appl. No.: 345,054

[22] Filed: Feb. 2, 1982

Related U.S. Application Data

[60] Division of Ser. No. 109,147, Jan. 2, 1980, abandoned, which is a continuation of Ser. No. 802, Jan. 4, 1979, abandoned.

[51] Int. Cl.$^3$ .................... A61K 39/02; C08B 37/00; C12P 19/04
[52] U.S. Cl. ........................................ 424/92; 424/88; 536/1.1; 435/101
[58] Field of Search ............... 424/92, 87, 88; 536/1; 435/253, 101

[56] References Cited

U.S. PATENT DOCUMENTS 4,207,414 6/1980 Kasper .................................. 424/87

OTHER PUBLICATIONS

Kasper, D., et al., J. Immunol., vol. 121, pp. 1096–1105, 1978.
Baker, C., et al., J. Exp. Med., vol. 143, pp. 258–270, 1976.
Baker, C., et al., J. Clin. Invest., vol. 61, pp. 1107–1110, 1978.
Baker, C., et al., Infect. and Immun., vol. 13, pp. 189–194, 1976.
Baker, C., et al., J. Inf. Dis., vol. 136, pp. 137–152, 1977.
Baker, C., et al., New England Journal of Medicine, vol. 294, pp. 753–756, 1976.
Russell et al., J. Immunol., vol. 109, pp. 90–96, 1972.
Lancefield et al., J. Hygcamb., vol. 64, pp. 191–203, 1966.
Wittner, et al., J. Bact., vol. 89, pp. 398–402, 1965.
Curtis et al., Fed. Proc., vol. 23, p. 191, 1964.
Lancefield, J. Exp. Med., vol. 67, pp. 25–40, 1938.
Lancefield, J. Exp. Med., vol. 59, pp. 441–457, 1934.

*Primary Examiner*—Blondel Hazel
*Attorney, Agent, or Firm*—Scully, Scott, Murphy & Presser

[57] ABSTRACT

Pure Group B Streptococcus antigen and Group B, Type III Streptococcus antigen are isolated, separated and purified from the culture medium in which the Group B, Type III Streptococcus are grown. The process involves (a) culturing the Group B, Type III Streptococcus in a nutrient medium, free of animal proteins and lipids, containing from 1 to 5% by weight glucose and from 0.04 M to 0.16 M phosphates; (b) separating the bacterial cells from the culture medium; (c) extracting and separating the Group B antigens and the Type III antigens from the culture medium supernatant by means of an anion exchanger; and, (d) purifying the resulting antigenic materials by chromatography on an agarose gel column. The antigens can be used as vaccines against infections caused by Group B or Group B, Type III Streptococcus.

6 Claims, No Drawings

GROUP B STREPTOCOCCUS ANTIGENS AND VACCINES

GOVERNMENT RIGHTS

The invention described herein was made in the course of work under a contract from the United States Department of Health, Education, and Welfare.

This is a divisional of application Ser. No. 109,147, filed Jan. 2, 1980 now abandoned which in turn is a continuation of Ser. No. 000,802, filed Jan. 4, 1979, now abandoned.

BACKGROUND OF THE INVENTION

Group B Streptococci have, in recent years, become known as a significant cause of serious neonatal infections. Clinically, two distinct syndromes have been recognized, i.e., "early onset" disease, beginning up to about five days after birth; and "late onset" disease, beginning about ten days to three months after birth.

Early onset disease is characterized by a high incidence of maternal complications. Pneumonia, respiratory distress syndrome, and bacteremia are common; whereas meningitis occurs in slightly less than one-third of the cases. Overall mortality is about 55%.

Late onset disease usually is not associated with maternal complications. About 75% of the late onset disease is meningitis. The infections of late onset disease are generally less severe than those of early onset disease. Overall mortality is about 25%.

Present data indicate that early onset disease occurs in about two per one thousand live births and late onset disease occurs in one per one thousand live births.

Group B Streptococci are classified into five serotypes on the basis of antigenic material extracted from the cell wall of the bacteria by hydrochloric acid. The serotypes are denoted Types Ia, Ib, Ic, II and III. Epidemiological studies to determine the incidence of maternal colonization suggest that as many as 25% of pregnant women harbor Group B Streptococcus as part of their normal vaginal flora. This flora consists of about 18–28% Types I, 34–44% Type II, and 33–37% Type III. Most of the early onset disease is caused by the same serotypes harbored by the mother, implying maternal-fetal transmission.

Group B, Type III Streptococcus strains cause about 80% of early onset meningitis and about 93% of late onset meningitis. Type III also causes about 90% of all late onset Group B Streptococcal infections.

Group B Streptococci cause the formation of antibodies in some women who are carriers of Group B Streptococci or who have had Group B Streptococcal infections. These antibodies are of several immunoglobulin types including the immunoglobulin G (IgG) type. This is manifested by the observation that uninfected neonates born of mothers with Group B Streptococcus antibodies have the same antibodies in their blood. This transplacental transfer of antibodies is a characteristic of IgG antibodies.

For many years a means of preventing Group B Streptococcal infections in pregnant women and neonates have been sought. A vaccine suitable for the purpose of immunizing women of childbearing age, particularly pregnant women, was sought, but until this invention was made, no one has been successful in producing a suitable vaccine, since no one has been able to prepare pure Group B or Type III antigens having the characteristics required for a successful vaccine.

The characteristics of a desirable vaccine against a bacterial disease are as follows:
(a) Immunize selectively against the bacterial antigen to prevent the disease for extended periods of time;
(b) Cause no undesirable reactions;
(c) Be monovalent; and
(d) Require low doses and one or two administrations.

In order to accomplish the preceding, it is necessary to obtain pure antigens which are specific to their antibodies and which can be obtained in a form sufficiently pure to cause no side reactions in the patient and of sufficient molecular size to elicit specific antibody production in humans. The antigens as well as the vaccine must be of sufficient purity so that no cross-reactions with human tissues occur.

Prior to this invention much research had been done with Group B Streptococci in attempt to isolate and purify the antigenic serological determinants of this bacteria. These attempts to obtain pure antigenic material resulted in the finding that each of the serotypes of Group B Streptococcus mentioned above has associated with it antigenic material reactive with Group B serological determinants (Group B antigen) as well as antigenic material reactive with the particular serotype serological determinant (Type antigen). It is known that with various process manipulations the Type antigens can be separated from the cell wall of the bacteria and then separated from the Group antigens. Both of these separations, according to the prior art, resulted in Group antigens which were not immunologically pure and, e.g., Type III, antigens which had immunological purity but did not have all the characteristics required to produce a desirable vaccine. Both the Type III and Group B antigenic serological determinants were found to be polysaccharides. As used herein, "serological determinants" means materials which are present in blood and have antigenic sites.

The prior methods of obtaining the antigens were directed to extraction from the intact cell or cell walls with hydrochloric acid, trichloracetic acid (TCA), hot formamide, or EDTA extraction followed by disruption of the bacterial cells by glass beads, enzyme digestion, and alcohol precipitation. These processes ultimately resulted in a "pure" Type III antigen. The Group B antigen resulting from these processes was generally associated with serotype antigenic activity such as Type III. None of these processes of the prior art is satisfactory for isolating both pure Type III antigen and pure Group B antigen, having the properties required to use in a vaccine with desirable characteristics. The Type III antigen is important since it can be used in a vaccine to immunize against the most serious diseases caused by the Group B Streptococcus.

It is thus apparent that there is a need for a method to produce pure Group B Streptococcus antigens and pure Type III Streptococcus antigens in such a form that they will be suitable for vaccines for humans to protect against infections caused by all serotypes of Group B Streptococci and Group, Type III Streptococcus.

BRIEF DESCRIPTION OF THE INVENTION

According to this invention, we have discovered a method of extracting and separating in pure form the Group B Streptococcus antigen and the Group B, Type III Streptococcus antigen from the supernatant of cultures of Group B, Type III Streptococci.

The Group B antigen reacts selectively with the Group B Streptococcus antibody. All the Group B Streptococcus serotypes share this Group B serological determinant.

The Type III antigen reacts selectively with the Group B, Type III Streptococcus antibody. The Type III antigen does not react with antibodies of the other Group B serotypes and does not react with the Group B antibody. The antibody to Group B, Type III antigen does not react with the serological determinant of the other Group B serotypes or the Group B antigen.

The Group B antigen is a polysaccharide which is composed of, on a dry weight basis, predominantly rhamnose, above about 60%, with some galactose and some glucosamine. The polysaccharide does not have any detectable sialic acid by our assay procedure, but does have phosphorylated sugar. The Group B antigen is negatively charged and is bound on a DEAE-cellulose ion exchanger equilibrated with a Tris buffer at pH 7.0. The antigen is elutible from the ion exchanger with the Tris buffer containing more than 0.02 M NaCl. In addition, the Group B antigen migrates anodally when subjected to immunoelectrophoresis.

The Type III antigen is a polysaccharide with is composed of, on a dry weight basis, about 25% sialic acid, about 15% glucose, about 30% galactose, and about 20% glucosamine, but does not contain rhamnose.

The method of producing the antigen involves (a) culturing the bacteria in a nutrient medium free of animal proteins, (b) separating the bacterial cells from the supernatant, (c) extracting and separating the Group B antigen and the Type III antigen from the supernatant growth medium by means of an ion exchanger, and (d) purifying the resulting antigenic materials by chromatography on an agarose gel column.

The antigens can be used as vaccines in sterile saline solution either as monovalent vaccines or mixed with each other and/or other compatible antigens to form di- or polyvalent vaccines.

DETAILED DESCRIPTION OF THE INVENTION

The Group B Streptococcus antigen and the Type III Streptococus antigen are isolated, separated and purified from Group B, Type III Streptococci culture media. Prior to inoculation into the culture medium, isolated colonies of Group B, Type III Streptococcus cultures are grown on blood agar plates. Any Group B, Type III Streptococcus can be used; for example, Type III strain D136C, which can be obtained from the American Type Culture Collection, Rockville, Md., under ATCC #12403. This invention, however, will be described using strain H732, which is available on unrestricted deposit in the American Type Culture Collection, Rockville, Md., under ATCC #31475.

In order to isolate pure high molecular weight material suitable for use in a vaccine for humans, it is necessary to culture the bacteria in a nutrient culture medium which will support good growth but will not contain any contaminating materials which could cause difficulties in eliciting proper antibody production or cause undesirable side effects in humans or animals. It is particularly important to use as a nutrient culture medium one which has no animal protein or lipids.

We have found that a chemically defined animal protein-free and lipid-free medium containing all those nutrients, e.g., vitamins, minerals, amino acids, salts, and carbohydrates needed for the bacteria to grow, having from about 1% to 5% by weight glucose and from about 0.04 M to 0.16 M phosphate in the form of alkali metal or alkaline earth metal phosphates and/or biphosphates are eminently satisfactory.

Any commercially available animal protein-free and lipid-free medium containing the proper ingredients is suitable. For purposes of this invention, a chemically defined culture medium in which, for convenience, acid hydrolyzed casein is substituted for many of the amino acids is preferred, since no animal proteins or lipids are present. Most preferred is a salt-free acid casein hydrolyzate at pH 7.0 containing about 5% by weight glucose and 0.16 M phosphates as potassium and sodium phosphates. The acid hydrolyzed casein is preferably salt-free in order to make it more convenient to adjust the salt content and concentration as desired. For example, a typical suitable acid hydrolyzed casein known as Humko Sheffield SF Casein Hydrolyzate, available from Humko Sheffield Chemical Co., Div. of Kraft, Norwich, N.Y., can be used in a culture medium that contains the following ingredients per 20 liters:

acid casein hydrolyzate adjusted to pH 7: 100 grams
1-glutamine: 6 grams
1-asparagine: 6 grams
monopotassium phosphate: 8.84 grams
dipotassium phosphate: 6.10 grams
ammonium sulfate: 12 grams
1-tryptophan: 2 grams
riboflavin: 16 mg
pantothenic acid: 34.4 mg
thiamine hydrochloride: 16 mg
PABA: 3.2 mg
nicotinamide: 80 mg
biotin: 0.4 mg
folic acid: 4 mg
pyridoxamine: 46 mg
glucose (5% aqueous sol.): 1,000 gm
$Na_2HPO_4$: 252 gm
$NaH_2PO_4$: 164 gm
sodium acetate: 120 gm
cysteine: 13 gm
$FeSO_4.7H_2O$: 400 mg
1-cystine: 4 gm
adenine sulfate: 435 mg
guanine hydrochloride: 310 mg
uracil: 250 mg
$MgSO_4.7H_2O$: 8,000 mg
NaCl: 400 mg
$MnSO_4.H_2O$: 302 mg
sodium citrate: 4.5 gm In order to reduce the chances of degrading any antigens present in the culture medium, it is necessary to incubate under mild conditions. It is for this reason that the incubation is carried out at about 34°–38° C. from about 12–72 hours, at neutral pH.

While the time required to incubate the bacteria is not critical, insufficient growth occurs in less than 12 hours and insignificant amounts of antigen are present in the supernatant. More than 72 hours of growth is inefficient and might be detrimental to the cells and antigens. Optimum growth is reached at the end of about 48 hours, the preferred incubation time.

The temperature at which the incubation takes place should be relatively low and the pH is neutral to avoid the harsh conditions known to degrade polysaccharide antigens.

The antigens are not extracted from the cells themselves according to this invention, because, as is demonstrated in the prior art processes, harsh conditions of either temperature or pH would be required.

Prior to incubating the bacteria in the culture medium, a starter culture is grown in a small aliquot of the nutrient culture medium. This starter culture medium is inoculated with sufficient Group B, Type III Streptococcus to provide about $10^{11}$ cells per 20 liters of the medium. Prior to use, filter sterilized sodium bicarbonate is added to the medium; then the starter culture is inoculated with the bacteria for several hours at about 34°–38° C.

The bacteria are obtained from frozen lyophilized cultures which have been streaked for purity on a blood agar plate.

The incubation is stopped by cooling the incubation medium to about 4° C. In order to avoid harsh conditions for isolating the antigens, only the antigenic material present in the culture medium is sought. This avoids the need to treat the bacterial cells to remove antigenic material. In addition, another advantage to isolating the antigenic material only from the culture medium is that because of the mild conditions these purified antigens are more likely to be similar to the antigens occuring in the bloodstream of an infected individual. Furthermore, the process of this invention results in a yield of antigens which is higher than can be obtained from cells or cell walls.

After the incubation is completed, the bacterial cells are removed by centrifugation, or filtration on an 0.45 micron filter. Filtration is the preferred method, since it removes all the cells; whereas after centrifugation some cells remain in the supernatant. These cells are collected and killed to avoid the possibility of the spread of infection. The supernatant is collected and tested by the capillary precipitation method using antiserum to Group B serological determinants produced in rabbits with Group B Streptococcus strain 090R (ATCC #12386), and antiserum to Type III produced in rabbits with Group B, Type III strain D136C (ATCC #12403), by the Lancefield method, Lancefield, J. Exp. Med. 59:441 (1934) and J. Exp. Med. 69:25 (1938). The test indicates whether Group B and Type III antigens are present. When Group B, Type III Streptococcus is cultured according to the process of this invention, the culture supernatant is found by the capillary precipitation test to contain materials which react with the Group B antiserum and the Type III antiserum.

The next process step, i.e., filtration concentration, is not critical to the success of this process, but is carried out for subsequent processing convenience. This step involves concentrating and dialyzing the supernatant using a 10,000 molecular weight filter. This filter is used because it was found that the larger filters, e.g., 100,000 molecular weight filters, are inadequate for this purpose, as they do not provide as much antigenic material which can be separated by charge into the Group and Type antigens. The reason for this is not known, since the antigens have an apparent molecular weight greater than 100,000. The filtration concentration can be accomplished with any convenient apparatus; for example, a Pellicon Cassette System available from Millipore Corporation, Bedford, Mass. The filtration concentration is carried out in the cold, about 4° C. In order to determine which solution contains the antigenic material after the filtration concentration step, both the materials containing less than 10,000 molecular weight and greater than 10,000 molecular weight are tested by the capillary precipitation method of Lancefield against the Group B antiserum and the Type III antiserum. The solution with material of less than 10,000 molecular weight contains no Group B or Type III specific antigens and is discarded. The solution with materials of greater than 10,000 molecular weight contains both Group B and Type III specific antigens. This latter solution is prepared for treatment by an ion exchange column by dialysis against distilled water which is gradually changed in composition by the slow addition of a buffer solution until the solution reaches a composition of buffer which is the same as that to be used in the subsequent ion exchange step. The identity of the buffer which is used is not critical to the process. However, the buffer should be of sufficiently low ionic strength at pH 7 to permit the negatively charged antigens to adhere to the ion exchange resin. For purposes of this invention, a Tris buffer can be used. The preferred Tris buffer used on the ion exchange column is one of 0.01 M Tris, pH 7.0. In order to achieve this buffer composition in the solution being dialyzed, a Tris buffer of 0.1 M is added until the solution reaches the desired buffer composition at pH 7. When this point is reached, the dialysis is completed.

It is not necessary to concentrate the filtrate from the culture medium, as it is possible to directly dialyze the filtrate or to add the ion exchanger to the medium. However, because of the volumes involved, it is more convenient to concentrate first. In most cases, the volume of culture medium is from about 20 liters to 100 liters. It is for this reason that the filtrate is concentrated to approximately 500 mls to two liters.

After the dialysis is completed, any soluble extracellular enzymes which may be present in the solution containing the antigens are destroyed by pasteurizing the solution at about 60° C. for about 30 minutes. This has no effect on the polysaccharide antigens.

We have found that the Group B antigens and Type III antigens present in the dialyzed solution can be isolated and separated in pure form by treating the dialyzed solution with an anion exchanger, then eluting the antigen with a linear salt gradient. The type of ion exchanger suitable for use is one which is positively charged, which will bind the Group B antigen and the Type III antigen, and then allow them to be eluted separately with a linear salt gradient.

The ion exchanger found suitable for use in accomplishing the desired separation is the anion exchanger diethylaminoethylcellulose (DEAE cellulose). The DEAE cellulose most suitable for use in this invention is the one which has a bead form gel-like structure, and a wet-bead diameter of about 40–160 micrometers. A suitable ion exchanger is available from Pharmacia, Inc., Piscataway, N.J., under the trademark DEAE-Sephacel.

The chromatography is accomplished by equilibrating the ion exchanger with 0.01 M Tris, pH 7.0, mixing it with the dialyzed Tris buffered solution of antigens, then pouring the mixture into a column. The eluates which originally run through the column and have no added salt in them do not have any antigen as determined by the capillary precipitation test.

In order to separate the antigens the column is eluted with a linear sodium chloride gradient of from 0–0.75 molar salt in 0.01 M Tris buffer, pH 7.0. Aliquots are collected in tubes and tested by capillary precipitation test to determine which, if any, antigen is present in the tube. The eluates are also tested for polysaccharides by the phenol-sulfuric assay for carbohydrates and for protein by the Lowry protein assay. In order to determine the concentration of salt in the buffer, electric conductivity tests are run on the eluates.

The Group B antigen eluted into tubes 16–35, i.e., a salt concentration of 0.02 M to 0.15 M. The Type III antigen eluted into tubes 45–55, i.e., a salt concentration of 0.15 M to 0.22 M. The column size was 2.4 cm×20 cm containing 100 ml of packed resin. Fractions collected contained approximately 8 ml.

The Group B and Type III active materials are prepared for purification on an agarose gel column by pooling the contents of the tubes containing Group B activity or type III activity. Each group of pooled material is then dialyzed against distilled water and a suitable buffer is added until the pooled materials contains the proper concentration of buffer at pH 7.0. The buffer is the same one used to equilibrate the agarose gel column and is also used as the eluate. The identity of the buffer is not critical, as long as it is at pH 7.0 and does not contain any materials which would contaminate the antigens. A convenient buffer is 0.2 M ammonium acetate, pH 7, which is preferred because it is easy to remove from the purified antigen. An 0.01 M Tris buffer pH 7.3 can also be used, but it is more difficult to remove from the antigens and is thus not the buffer of choice.

The antigens are then purified further by subjecting them separately to column chromatography on an agarose gel column. This separates those materials with molecular sizes greater than 30,000 from smaller molecular weight materials. Agarose is the neutral portion of agar. The gel material is commercially available from Pharmacia, Inc., Piscataway, N.J., under the trade name Sepharose. The gels are available as aqueous suspensions in 0.02% azide as preservative. The gel structure is due to hydrogen bonding. The gel is prepared in beaded form having a selected particle size and percent agarose. The concentration of the agarose in the gel determines the fractionation range. The gels most suitable for use in this invention are those which have a particle size of from 40–190 microns and contain 4% by weight agarose. These materials, named Sepharose 4B, have a fractionation range of $3\times10^4$ to $5\times10^6$. In the process of this invention, Sepharose 4B is used, since it permits separation of the Type III and Group B fractions from extraneous materials of higher and lower molecular weight as well as colloidal particles. The columns used generally are from 2.25×80 cm to 2.5×100 cm, with a volume of 400 ml. The column is eluted with an 0.2 M ammonium acetate buffer, pH 7, and fractions are collected in tubes. The antigen is detected in the tubes by phenol-sulfuric assay for carbohydrates, capillary precipitation, and the Lowry protein assay.

The Type III antigens are collected in fractions 46–69 and 70–79. Since the earlier fractions contain less protein, they are kept separately.

The Group B antigen, which is treated separately but identically, is chromatographed in exactly the same way as the Type III antigen, and is collected in fractions 70–87 and 90–95. It is essentially protein-free. The purified antigens are stored at −70° C. until ready for use.

The purified Group B antigenic material is a polysaccharide, which is composed of, on a dry weight basis, about 70% rhamnose, about 20% galactose, about 10% glucosamine, and about 2.1% phosphorus. In addition, there is a very small amount of protein 1.2%.

The pure Group B antigenic material reacts selectively with the Group B antibodies as evidenced by the fact that it forms a single line precipitate with its specific antibody in unabsorbed Group B Streptococcus antiserum in gel diffusion tests and immunoelectrophoresis, is water soluble and is free of any Type III antigenic material.

In addition to the above characteristics, the pure Group B antigen is bound by a positively charged ion exchanger equilibrated with an 0.01 M Tris buffer pH 7.0, and is elutable from the ion exchanger with an 0.01 M Tris buffer, pH 7.0, containing from 0.02 M to 0.15 M sodium chloride. When subjected to agar gel immunoelectrophoresis using 30 milliamps, with a barbitol buffer of pH 8.6 and ionic strength of 0.075, the Group B antigen migrates anodally from 0.4 to 2.3 cm at the same time a bromophenol tracking dye migrates 5 cm anodally.

The pure Group B antigen is elutable from an agarose gel column as described herein with an 0.2 M ammonium acetate buffer, pH 7. Under these conditions, the apparent molecular size of the Group B antigen is 125,000 to 150,000.

The pure Type III antigenic material is a polysaccharide which is composed of, on a dry weight basis, glucose 15%, galactose 30%, glucosamine 20%, sialic acid 25%, and a small amount of protein, 2.1%. The type III antigenic material contains no rhamnose. The pure Type III antigenic material reacts selectively with Type III antibodies, as evidenced by the fact that it forms a single line precipitate with its specific antibody in unabsorbed Group B, Type III Streptococcus antiserum in gel diffusion tests and immunoelectrophoresis, is soluble in water and is free of Group B antigen.

In addition to the above characteristics, the pure Type III antigen is bound by a positively charged ion exchanger equilibrated with an 0.01 M Tris buffer, pH 7.0, containing from 0.15 to 0.22 M sodium chloride. When subjected to agar gel immunoelectrophoresis, using 30 milliamps with a barbitol buffer of pH 8.6 and ionic strength of 0.075, the Type III antigen migrates anodally from 1.2 to 2.3 centimeters at the same time a bromophenol tracking dye migrates five centimeters anodally.

The pure Type III antigen is elutable from an agarose gel column as described herein, with an 0.2 molar ammonium acetate buffer, pH 7. Under these conditions the apparent molecular size of the Type III antigen is 100,000 to 200,000. When the Type III antigen is eluted from an agarose gel column with an 0.01 M Tris buffer, pH 7.3, the apparent molecular size is 500,000 to 600,000.

Each of the antigens isolated and purified according to this invention meets the criteria for use as a vaccine in humans.

A vaccine containing Group B antigen can be used to immunize patients against all Group B Streptocccus infections. The patients most in need of such protection are women of childbearing age, although others in danger of infection from Group B Streptococcus can also be immunized.

The dosage of vaccine and frequency of administration can vary according to the condition and needs of the patient in the judgment of the clinician.

Generally the dose can vary from about 50–250 micrograms in 0.1–0.5 ml sterile physiological saline administered intramuscularly. In ordinary cases, one or two administrations are sufficient to elicit production of an adequate amount of antibodies.

The Type III antigen can also be used as a vaccine, but it is only effective against Group B, Type III Streptococcus infections. The same dosage and administration regimen is used for the Type III as for the Group B vaccines.

In some instances, in the judgment of the clinician, it might be necessary to make a bivalent vaccine containing both Group B and Type III antigens or a mixed Group B, Types I, II, and/or III antigens. The dosages and administration regimens would be the same as for the monovalent vaccines. However, the relative amounts of Group B and Type III antigens would be set according to the judgment of the clinician. In most cases, the antigens would each be present in from about 50–250 micrograms per dose.

The antigens can also be used as components of polyvalent vaccines containing antigens which are compatible with the Group B and Type III polysaccharides, each antigen being present in the amount required for its effectiveness.

The following examples illustrate the invention.

EXAMPLE 1

Three liters of distilled water and 20 grams of Humko Sheffield SF casein hydrolyzate (a salt-free, animal protein-free acid casein hydrolyzate available from Sheffield Chemical Co., Norwich, N.Y.) were put into each of five 6 liter flasks; the pH was adjusted to 7 with 2.5 N NaOH. A 75 ml aliquot was removed from one of the flasks and put into a smaller flask. All the flasks were then put into an autoclave and autoclaved for 15 minutes at 15 lbs. pressure, after which they were cooled to room temperature (i.e., about 20°–25° C.). The contents of the 6 liter flasks were combined to form a 20 liter culture medium. The following were put into 5 liters of distilled water: 6 gm of l-glutamine; ≠gm of l-asparagine; 8.8 gm of potassium monophosphate; 6.10 gm of potassium diphosphate; 12 gm of ammonium sulfate; 2 gm of l-tryptophan; 16 gm of riboflavin; 34.3 mg of pantothenic acid; 16 mg of thiamine hydrochloride; 3.2 mg of PABA; 80 mg of nicotinamide; 0.4 mg of biotin; 4 mg of folic acid; 46 mg of pyridoxamine; 1,000 gm of glucose; 252 gm of sodium hydrogen phosphate; 164 gm of sodium dihydrogen phosphate; 120 gm of sodium acetate; 13 gm of cysteine; 4 gm of l-cystine; 8,000 mg of $MgSO_4.7H_2O$; 400 mg of NaCl; 400 mg of $FeSO_4.7H_2O$; 302 mg of $MnSO_4.H_2O$; 435 mg of adenine sulfate; 310 mg of guanine hydrochloride; 250 mg of uracil; and 4.5 gm of sodium citrate. The pH of this mixture was adjusted to 7 with 2.5 N NaOH. The solution was filter sterilized on an 0.45 micron Millipore filter.

25 ml of the sterile vitamin solution was added to the 75 ml aliquot of casein hydrolyzate and, if necessary, the pH can be adjusted to 7 with sterile 2.5 N NaOH. The resulting solution is the starter culture medium. The remaining sterile vitamin solution was mixed into the 20 liter culture medium.

Isolated colonies of Group B, Type III Streptococcus culture M732 (ATCC #31475) were grown on a blood agar plate 24 hours prior to inoculation of the 20 liter culture medium. Six hours before the inoculation of the 20 liter culture medium, approximately ten (10) colonies of the M732 culture were taken from the blood agar plate and the organisms were inoculated into 100 ml of the starter medium. The culture mediums were prepared for inoculation by adding 200 ml filter sterilized solution of sodium bicarbonate (0.84 gm/10 ml) to the 20 liter medium and 1 ml to the 100 ml medium. The inoculated medium was incubated for six hours at 37° C. The incubated suspension of the starter culture was then inoculated into the 20 liter culture medium and incubated at 37° C. for about 48 hours without shaking.

The growth was stopped by cooling the culture medium and keeping it on ice at about 4° C. The bacterial cells were separated from the culture medium by filtering on an 0.45 micron filter. The filtering was done in the cold, about 4° C.

The cells were collected from the filter by centrifugation at up to 8,000 rpm for 25 minutes. The cells were then pasteurized at 60° C. for about 30 minutes. The heat inactivated cells were then lyophilized.

The filtrate from the culture medium was tested by the capillary precipitation test to determine if there were any Group B and/or Type III antigens present. The test was carried out as follows. A capillary tube was partially filled with antiserum for Group B antigen and then dipped into the filtrate where a small amount was drawn up into the capillary tube. At the interface of the filtrate and antiserum a precipitate formed. This precipitate indicated that Group B antigens were present in the filtrate. The capillary precipitation test was also carried out using antiserum for Type III antigen, and the results showed that Type III antigen was also present in the filtrate. The antiserums used in these assays were produced according to the Lancefield method.

The filtrate was then concentrated by filtering on a Pellicon Filter Cassette with 10,000 molecular weight filters. This reduced the 20 liter volume to approximately 500 ml. The retentate was then pasteurized at 60° C. for 30 minutes, in order to denature any extracellular enzyme which might be present. The liquid that did pass through the filter, i.e., materials with molecular weight less than 10,000 were tested by the capillary precipitation test for the presence of Group B antigen and Type III antigen. There were no Group B or Type III antigens detected in the material with less than 10,000 molecular weight. The material which was retained on the 10,000 molecular weight filter was also tested by the capillary precipitation test for Group B and Type III antigens. Both Group B and Type III antigens were found present. The retentate containing the Group B and Type III antigens was dialyzed against distilled water, and then the contents of the dialysis bag were buffered by adding increments of 0.1 M Tris until the retentate contained 0.01 M Tris, pH 7.0. At this point the dialysis was completed and stopped.

EXAMPLE 2

The column containing DEAE-Sephacel was prepared as follows. The DEAE-Sephacel, which is supplied pre-swollen in suspension in 0.5 NaCl solution containing denatured ethanol was decanted, then washed with 100 ml of 0.01 M Tris, pH 7.0 buffer. This suspension was centrifuged until the DEAE-Sephacel packed down to 100 ml. The DEAE-Sephacel was then suspended in aqueous solution and washed with 400 ml of the same Tris buffer. This equilibrates the ion exchange resin. The equilibrated ion exchange resin was added to the solution from Example 1 and allowed to sit for at least 24 hours at 4° C. The DEAE-Sephacel-antigen mixture was poured into a column of the following dimensions: 2.4 cm × 20 cm. The antigens were eluted with a linear sodium chloride gradient using 1,200 ml of buffer having from 0 to 0.7 M NaCl. Fractions containing about 8 ml were collected in separate tubes and the fractions were each tested by the capillary precipitation test for the Group B and Type III antigens. The Group B antigen was found in fractions 16–35, which correspond to a sodium chloride concentration of about 0.02 to 0.15 M NaCl. The Type III antigen was found in fractions 45–55, which correspond to a sodium chloride concentration of about 0.15 to 0.22 M NaCl. The fractions containing the Group B antigen were pooled, and the fractions containing the Type III antigen were pooled. The pooled fractions of each of the antigens were dialyzed against 0.2 M sodium acetate, pH 7, buffer and concentrated to about 5 ml.

The Group B antigen pool was subjected to chromatography on a Sepharose 48 column (2.5×80 cm col.=400 ml) previously equilibrated with 0.2 M ammonium acetate, pH 7. Approximately 4 ml fractions were collected and the presence of the Group B antigen in the fractions was detected by the phenolsulfuric assay for carbohydrates, the capillary precipitation test and the Lowry protein assay. The Group B specific antigen was found in fractions 79–87 and 90–95. The buffer used for the elution was 0.2 M ammonium acetate pH 7. The fractions were pooled and dried to yield 0.104 gm of a white powder. The purified antigens were kept at −70° C. until ready for use.

EXAMPLE 3

The Type III antigen pool from Example 2 was chromatographed in the same manner as the Group B antigen pool in Example 2, using the same volumes and the same column. This antigen was found in fractions 46–69 and 70–79. The earlier fractions contain less protein and were kept separately from later fractions. To determine the yield the earlier fractions were pooled and dried and the later fractions were pooled and dried to give a combined yield of 0.035 gms of the Type III antigen as a white powder. The purified antigens were kept at −70° C. until ready for use.

EXAMPLE 4

Using the methods described in Examples 1, 2 and 3, but changing the composition of the growth medium, as shown below, with an incubation time of 18 hours at 37° C., the indicated yields were obtained.
 (a) Changes in media
  glucose 1% aqueous solution: 200 gm/20 l.
  $Na_2HPO_4$: 63 gm/20 l.
  $NaH_2PO_4$: 41 gm/20 l.
 (b) Yields/20 l.
  (i) Batch A
   Group B antigen: 28.8 mg
   Type III antigen: 11.3 mg (combined early and late eluates)
  (ii) Batch B
  Group B antigen: 33.3 mg
  Type III antigen: 16.4 mg (combined early and late eluates)

EXAMPLE 5

(a) The product from Example 2 was tested in a gel diffusion test against unabsorbed Group B Streptococcus antiserum. A single line precipitate formed. The product was also subjected to agar gel immunoelectrophoresis, using 30 milliamps with a barbital buffer, pH 8.6, ionic strength 0.075 and a bromophenol tracking dye. The product migrated 0.4 to 2.3 cm anodally at the same time the bromophenol tracking dye migrated 5 cm anodally. The product was also analyzed chemically and found to have, on a dry weight basis, 70% rhamnose, 20% galactose, 10% glucosamine and 2% phosphorus. No sialic acid was detected. The above confirmed the product was pure Group B antigen.

(b) The product from Example 3 was tested in a gel diffusion test against unabsorbed Group B, Type III Streptococcus antiserum. A single line precipitate formed. The product was also subjected to agar gel immunoelectrophoresis, using 30 milliamps with a barbitol buffer, pH 8.6, ionic strength 0.075 and a bromophenol tracking dye. The product migrated anodally 1.2 to 2.3 cm at the same time a bromophenol tracking dye migrated 5 cm anodally. The product was also analyzed chemically and found to have, on a dry weight basis, 25% sialic acid, 15% glucose, 30% galactose, 20% glucosamine and 2.1% protein. No rhamnose was detected. The above confirmed the product was pure Group B, Type III antigen.

EXAMPLE 6

(a) A vaccine was prepared as follows. Solutions of pure Group B antigen, prepared according to Example 2, in sterile saline were prepared so that there was a concentration of 50 micrograms of Group B antigen per 0.1 ml of sterile saline. 0.1 ml of the solution was put in an ampule for injection. Other solutions containing from 50–250 micrograms of Group B antigen per 0.1 to 0.5 ml of sterile saline were prepared and added to ampules for injection of 0.1 ml capacity and 0.5 ml capacity. Similar compositions for vaccines were made with pure Type III antigens prepared according to Example 3.

(b) A divalent vaccine containing 50–250 micrograms each of pure Group B antigen and pure Type III antigen per 0.1 to 0.5 ml of sterile saline were prepared and were put into ampules for injection.

We claim:

1. A process for producing pure Group B Streptococcus antigen and the pure Type III Streptococcus antigen of Group B Streptococcus which comprises:
 (a) growing Group B, Type III Streptococcus in a nutrient culture medium at pH 7 which is free of animal protein and lipids and which contains essential nutrients, including from about 1% to 5% by weight glucose and about 0.04 M to 0.16 M phosphate, at about 34° to 38° C. for from about 12 to 72 hours.
 (b) cooling the culture medium to about 4° C.;
 (c) removing the bacterial cells from the culture medium;
 (d) dialyzing the culture medium produced in step (c) against distilled water, while adding sufficient buffer to provide the equivalent of 0.01 Tris, pH 7.0;
 (e) treating the buffered dialyzed culture medium with an anion exchanger equilibrated with the same buffer as in the medium, to thereby bind the negatively charged Group B and Type III antigens;
 (f) eluting from the ion exchanger with a linear sodium chloride gradient of 0 to 0.75 M sodium chloride in the same buffer whereby the Group B antigen is eluted at 0.02 to 0.15 M sodium chloride, and the Type III antigen is eluted at 0.15 to 0.22 M sodium chloride;
 (g) collecting each of Group B antigen and Type III antigen separately and buffering each with a buffer at pH 7, then eluting each through an agarose gel column containing 4% by weight of agarose, having a particle size of 40 to 190 microns and a fractionation range of $3 \times 10^4$ to $5 \times 10^6$ with the same buffer, and collecting pure Group B antigen and pure Type III antigen.

2. The process of claim 1, wherein the nutrient culture medium is an acid hydrolyzed casein containing 5% by weight glucose and 0.16 M phosphate.

3. The process of claim 1, after step (c) and before step (d), wherein the culture medium from step (c) is concentrated on a 10,000 molecular weight filter apparatus.

4. The process of claim 1, steps (d), (e), and (f), wherein the buffer is 0.01 M Tris, pH 7.0.

5. The process of claim 1, wherein in step (e) the ion exchanger is a DEAE-cellulose.

6. The process of claim 1, wherein the step (g) the buffer is 0.2 M ammonium acetate, pH 7.

* * * * *

UNITED STATES PATENT AND TRADEMARK OFFICE
CERTIFICATE OF CORRECTION

PATENT NO. : 4,439,422
DATED : March 27, 1984
INVENTOR(S) : Robert M. Swenson, et al.

It is certified that error appears in the above-identified patent and that said Letters Patent are hereby corrected as shown below:

Col. 3, line 55, "H732" should read as --M732--

Col. 9, line 38, "$\cancel{\ }$gm" should read as --6gm--

Col. 11, line 16, "48 column" should read as --4B column--

Signed and Sealed this

Twelfth Day of March 1985

[SEAL]

Attest:

DONALD J. QUIGG

Attesting Officer    Acting Commissioner of Patents and Trademarks